(12) United States Patent
Duespohl et al.

(10) Patent No.: US 10,048,238 B2
(45) Date of Patent: Aug. 14, 2018

(54) METHOD OF MONITORING PRODUCTION OF A CHEMICAL PRODUCT AND A CHROMATOGRAPH USED THEREWITH

(71) Applicant: Union Carbide Chemicals & Plastics Technology LLC, Midland, MI (US)

(72) Inventors: Dale Duespohl, Hurricane, WV (US); Robert Reib, Hurricane, WV (US); John Parrish, Charleston, WV (US)

(73) Assignee: Union Carbide Chemicals & Plastics Technology LLC

( * ) Notice: Subject to any disclaimer, the term of this patent is extended or adjusted under 35 U.S.C. 154(b) by 0 days.

(21) Appl. No.: 15/322,122

(22) PCT Filed: Jun. 15, 2015

(86) PCT No.: PCT/US2015/035741
§ 371 (c)(1),
(2) Date: Dec. 26, 2016

(87) PCT Pub. No.: WO2015/200019
PCT Pub. Date: Dec. 30, 2015

(65) Prior Publication Data
US 2017/0146499 A1    May 25, 2017

Related U.S. Application Data

(60) Provisional application No. 62/018,186, filed on Jun. 27, 2014.

(51) Int. Cl.
*G01N 30/86* (2006.01)
*G01N 30/88* (2006.01)
*C08F 210/16* (2006.01)
*C08F 2/34* (2006.01)

(52) U.S. Cl.
CPC ....... *G01N 30/8658* (2013.01); *C08F 210/16* (2013.01); *G01N 30/88* (2013.01); *G01N 2030/8886* (2013.01)

(58) Field of Classification Search
CPC ........... G01N 30/88; G01N 2030/8886; G01N 30/8658; C08F 2/34; C08F 210/06

USPC ............................ 526/59; 73/23.38; 436/161
See application file for complete search history.

(56) References Cited

U.S. PATENT DOCUMENTS

| 4,469,853 A  | * | 9/1984  | Mori ................... B01J 8/001 |
|              |   |         | 526/59 |
| 6,365,681 B1 |   | 4/2002  | Hartley et al. |
| 7,346,469 B2 |   | 3/2008  | Taware et al. |
| 7,720,641 B2 |   | 5/2010  | Alagappan et al. |
| 8,032,328 B2 |   | 10/2011 | Samples et al. |
| 8,121,817 B2 |   | 2/2012  | Landells et al. |
| 8,354,481 B2 |   | 1/2013  | Samples et al. |
| 8,742,035 B2 |   | 6/2014  | Samples et al. |
| 2010/0127860 A1 |   | 5/2010  | Ganguly et al. |
| 2013/0069792 A1 |   | 3/2013  | Blevins et al. |

FOREIGN PATENT DOCUMENTS

| WO | 2006/049857 A1 | 5/2006 |
| WO | 2014/039519 A1 | 3/2014 |

OTHER PUBLICATIONS

Model-Based and Data Driven Fault Diagnosis Methods with Applications to Process Monitoring, Qingsong Yang, PhD Thesis, Case Western Reserve University, May 2004.
PCT/US2015/035741, International Preliminary Report on Patentability dated Dec. 27, 2016.
PCT/US2015/035741, International Search Report dated Dec. 30, 2015.
PCT/US2015/035741, Written Opinion dated Dec. 30, 2015.

* cited by examiner

*Primary Examiner* — Fred M Teskin (57) ABSTRACT

A method for monitoring a chromatograph used to control production of a chemical product. The method involves sampling a chemical mixture of chemical components used during the production to form the chemical product, measuring the composition of the sample with a chromatograph and adjusting the amount of the chemical components based on the measured composition. The method also involves measuring actual parameters of the sample with at least one gauge, determining expected parameters of the sample based on the measured composition and the measured actual parameters using an equation-of-state, and detecting a fault in the chromatograph by comparing the expected parameters with the actual parameters.

10 Claims, 6 Drawing Sheets

METHOD OF MONITORING PRODUCTION OF A CHEMICAL PRODUCT AND A CHROMATOGRAPH USED THEREWITH

BACKGROUND

The instant disclosure relates generally to techniques for producing products, such as polymers or other chemicals. More specifically, the instant disclosure relates to techniques for monitoring chemical processes and equipment.

Polymers may be produced by passing certain chemicals through a production process. Chemicals, such as ethylene, hydrogen, and nitrogen, and comonomers may be purified and passed through a reactor and combined with a catalyst to form a resin. The resin may then be packaged into a product for use in products, such as films. In some cases, additives may be incorporated into the resin to achieve the desired product.

Techniques have been developed for producing polymers. Examples of various aspects of polymer production are provided in U.S. Pat. Nos. 8,032,328, 6,365,681, 8,354,481, and 8,742,035, the entire contents of which are hereby incorporated by reference herein.

SUMMARY

In at least one aspect, the disclosure relates to a method for monitoring a chromatograph used to control production of a chemical product. The method involves sampling a chemical mixture of chemical components used during the production to form the chemical product, measuring a composition of the sample with a chromatograph and adjusting the amount of the chemical components based on the measured composition, measuring actual parameters of the sample with at least one gauge, determining expected parameters of the sample based on the measured composition and the measured actual parameters using an equation-of-state, and detecting a fault in the chromatograph by comparing the expected parameters with the actual parameters.

In another aspect, the disclosure relates to a method for monitoring production of a chemical product formed from chemical components. The method involves forming a chemical mixture by passing the chemical components through a reactor, controlling the forming, and monitoring the controlling. The controlling involves collecting a sample of the chemical mixture during the forming, determining a composition of the sample with a chromatograph during the forming, and adjusting the passing of at least one of the chemical components through the reactor based on the determining. The monitoring involves measuring actual parameters of the sample, determining expected parameters of the sample based on the determined composition and the measured actual parameters using an equation-of-state, comparing the expected parameters with the actual parameters of the sample, and adjusting the controlling based on the comparing.

Finally, in another aspect, the disclosure relates to a method for monitoring production of a chemical product. The method involves forming a chemical mixture by passing chemical components through a reactor, controlling production of a chemical product, and detecting fault in the chromatograph. The controlling involves sampling a chemical mixture of chemical components used during the production to form the chemical product, measuring a composition of the sample with a chromatograph, and adjusting the amount of the chemical components based on the measured composition. The detecting involves measuring actual parameters of the sample with at least one gauge, determining expected parameters of the sample based on the measured composition and the measured actual parameters using an equation-of-state, comparing the expected parameters with the actual parameters, adjusting the controlling based on the detecting.

BRIEF DESCRIPTION OF THE DRAWINGS

For the purpose of illustrating the disclosure, there is shown in the drawings a form that is exemplary; it being understood, however, that this disclosure is not limited to the precise arrangements and instrumentalities shown.

DETAILED DESCRIPTION

The description that follows includes exemplary apparatus, methods, techniques, and/or instruction sequences that embody techniques of the present subject matter. However, it is understood that the described embodiments may be practiced without these specific details.

The present disclosure relates to the monitoring of production of a chemical product (e.g., a polymer) and/or monitoring a chromatograph used therewith. The production process may involve reaction of chemical components, such as chemicals (e.g., Ethylene, Nitrogen, Hydrogen), a comonomer, and a catalyst, to form a chemical mixture. During reaction, a sample of the chemical mixture may be taken to detect a composition thereof using a chromatograph. The term chromatograph as used herein refers generally to all devices capable of measuring composition of a chemical mixture, such as a gas chromatograph or gas composition analyzer.

Based on this monitoring, the production process and/or chemical composition may be altered, for example by adjusting flow rates of chemical components at input. Actual parameters of the sample may also be measured and compared with expected parameters determined from the detected composition. The comparison may be used to detect a fault in the chromatograph. In cases where the chromatograph is used to control the production, the chromatograph may be adjusted where a fault is detected, or an alternative control may be used.

Figure 1:
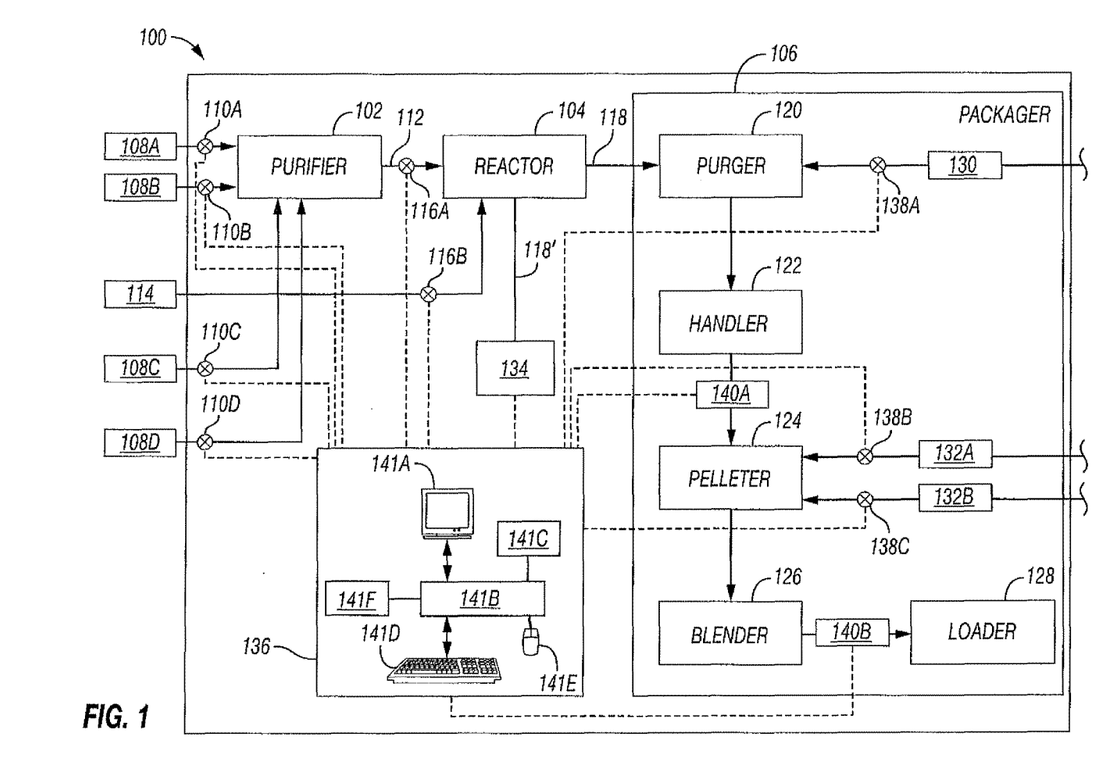
FIG. 1 is a schematic diagram depicting production of a chemical product and a monitor used therewith.

FIG. 1 is a schematic diagram depicting production 100 of a chemical product, such as a polymer, and monitoring of such production. In the example of FIG. 1, specific chemical components, such as gasses (e.g., Ethylene, Nitrogen, Hydrogen), comonomers, catalysts, and additives, are depicted as inputs used to form the chemical product. The monitoring used in FIG. 1 may be used with the depicted production, or other chemical processes.

As shown in FIG. 1, production involves purification by a purifier 102, reaction by a reactor 104, and packaging by a packager 106. The purification involves the receipt of various chemical components, such as ethylene 108$a$, hydrogen 108$b$, nitrogen 108$c$, and a comonomer 108$d$, via respective intakes (e.g., valves) 110$a$-$d$. While specific chemical components are depicted, a variety of chemical components may be input for purification, such as a condensing agent (e.g., isopentane). Purification may be performed using one or more conventional purifiers 102, such as a hydrogen purifier or filtration unit, to remove contaminants and/or undesirable items from the chemical components and/or to generate a purified chemical component, collectively referred to by reference number 112.

The reactor 104 involves the receipt of the purified chemical components 112 from the purifier 102 and a catalyst 114. The purified chemical components 112 and the catalyst 114 may be provided to the reactor 104 via controllers 116$a$,$b$. The reactor 104 may be, for example, a gas phase fluidized bed reactor used to react molecules of the chemical components 112 while generating a chemical reaction with the catalyst 114 to form a chemical mixture (e.g., a resin) 118. Examples of reactors are provided in U.S. Pat. Nos. 8,742,035 and 8,354,481, previously incorporated by reference herein.

The chemical mixture 118 is passed to the packager 106 for packaging and processing for use. The packaging 106 may involve, for example, altering the shape and structure of the chemical mixture into a usable product. As shown, the packaging may involve one or more of: purging with a purger 120, granular handling with a handler 122, pelleting with a pelleter 124, pellet blending with a blender 126, and loading with a loader 128. Purging 120 may involve cleaning the chemical mixture 118. Additional chemical components, such as Nitrogen 130, may be added at purging 120. Granular handling 122 may involve shaping the chemical mixture into granules for transport or use.

Pelleting 124 may involve shaping the granules into pellets. During pelleting 124, additives, such a dry additives 132$a$ and/or liquid additives 132$b$ may optionally be added. Pellet blending 126 may involve blending of one or more pellets and/or other additives. The final product may then be loaded 128 for transport. Loading 128 may involve packaging in containers, storage bins, transporters, or other devices for later use.

As also shown in FIG. 1, the production 100 may also include a monitor 134 and at least one controller 136. The controller(s) 136 may be part of the monitor 134 and/or separate therefrom. The monitor 134 is operatively connected to the reactor 104 for receiving a sample 118' of the chemical mixture 118. The monitor 134 is operatively connectable to the controller 136 for passing data thereto. The controller 136 is operatively connectable to the various valves 110$a$-$d$ and 116$a$-$b$ for sending command signals thereto based on the data received from the monitor 134. Communication with the controller 136 and various components, such as valves 110$a$-$d$, 116$a$-$b$, 138$a$-$c$, and monitor 134, is schematically depicted by dashed lines.

Additional valves 138$a$,$b$,$c$ may be provided about the production 100 to permit control thereof by the controller 136. Inspectors 140$a$,$b$ are also depicted as providing data to the controller 136. The inspectors 140$a$,$b$ may be, for example, sensors or other devices capable of measuring product parameters of the produced polymer in its various formats. For example, an inspector 140$a$ may be provided to measure weight, size, content, or other parameters of the granulized polymer generated from the granular handling 122. This information may be fed back to the controller 136 for analysis and/or adjustment.

The controller 136 as shown is a computer with a monitor 141$a$, central processing unit (CPU) 141$b$, communicator 141$c$, keyboard 141$d$, mouse 141$e$, and database 141$f$. The controller 136 may be operatively connected to various portions of the production 100 as shown for communication therewith via communicator 141$c$. Communicator 141$c$ may be, for example, networks, cables, wireless links, transceivers or other communication device. Collected data may be stored in the database 141$f$ and passed to the CPU 141$b$ for processing.

The controller 136 may be used to receive and analyze data, and send control commands in response thereto. The controller 136 may work with, for example, pre-existing software capable of activating the controls of the various valves 110$a$-$d$, 116$a$-$b$, 138$a$-$c$, or other portions of the process based on input data. Examples of software usable for controlling a production process include APC+™ commercially available from UNIVATION (see: www.univation.com) and UNIPOL UNIPPAC™ Advanced Process Control software commercially available from W.R. GRACE & CO.™ (see:www.grace.com).

Figure 2:
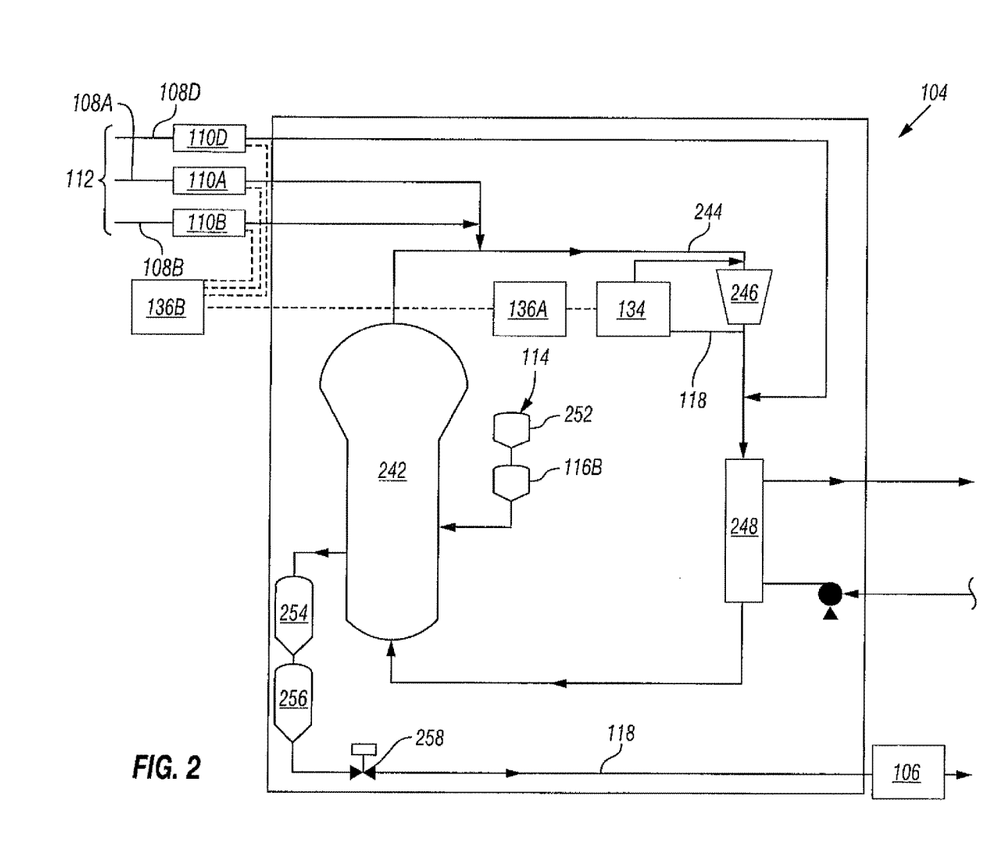
FIG. 2 is a schematic diagram depicting a reactor of FIG. 1 in greater detail.

FIG. 2 is a schematic diagram depicting reaction by reactor 104 of FIG. 1, and monitoring using monitor 134. While FIG. 2 shows an example of a reactor 104, the monitor 134 may be used with various reactors or other portions of the production 100. Examples of reactors and associated apparatuses and methods are provided in U.S. Pat. No. 8,742,035, previously incorporated by reference herein.

As shown in this diagram, the reaction 104 includes a reactor unit 242 and a flow circuit 244. The flow circuit 244 provides a fluid path for passage of the purified chemical components 112 (purified chemical components 108$a$-$d$) into the reactor unit 242. The purified chemical components 112 are recirculated through the reactor unit 242 via the flow circuit 244 and mixed with catalyst 114 to form the chemical mixture. The reactor unit 242 may be used to create a reaction in the chemical mixture to form a resin.

A cycle gas compressor 246 and a cycle gas cooler 248 are provided along the flow circuit 244. The gas compressor 246 may be a conventional gas compressor capable of selectively pressurizing and/or heating the chemical components 112. The cycle gas cooler 248 may be a conventional cooler, such as a heat exchanger with a pump to circulate a cooling fluid therethrough.

The monitor 134 is operatively connectable to the fluid circuit 244 for taking samples 118' of the recirculated chemical components 112 that is formed into the chemical mixture 118. As shown, the monitor 134 is coupled about the cycle gas compressor 246 to selectively drawn from the fluid circuit 244 and dump fluid back to the fluid circuit 244 as shown by the arrows.

As also shown in FIG. 2, the monitor 134 may be coupled to one or more internal and/or external controllers 136$a$,$b$ for performing analysis and/or sending commands. In this example, internal controller 136$a$ is used to collect measurements and perform analysis, and external controller 136$b$ is provided for receiving data and sending control commands to the valves 110$a$-$d$ to control flow of the chemicals into the reactor 104. This control may be used, for example, to adjust composition of the recirculated chemical components 112 as they are formed into the chemical mixture 118.

The reaction 104 may also include a catalyzer hold tank 252 for storing the catalyst 114 therein, and a catalyzer feeder (or controller) 116$b$ to selectively disperse the catalyst to the reactor unit 242. A product chamber 254 and a product blow 256 may be provided to collect, store and cool the chemical mixture 118 produced by the reaction 104. Valve 258 may be provided to selectively release the chemical mixture 118 to packager 106.

Figure 3:
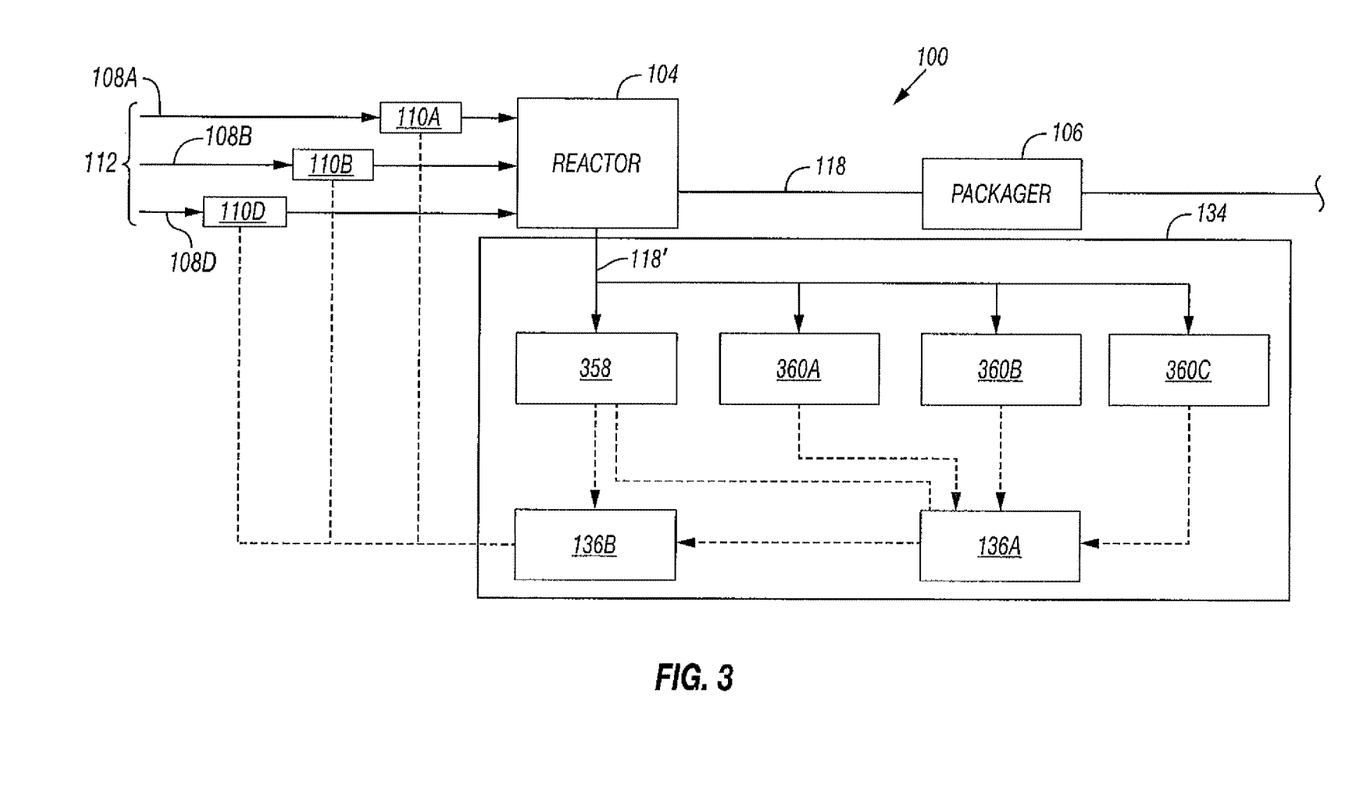
FIG. 3 is a schematic diagram depicting the monitor of FIG. 1 in greater detail.

FIG. 3 is a schematic diagram depicting another view of the production 100 with the monitor 134 shown in greater detail. As shown in this view, the monitor 134 is operatively connected to the reactor 104 to receive a sample 118' of the chemical mixture 118 therefrom. The monitor 134 includes a chromatograph 358, gauges 360a-c, and the controllers 136a,b. The chromatograph 358 may be, for example, a conventional gas chromatograph capable of detecting composition of a fluid. The chromatograph 358 is operatively connected to the reactor 104 to receive the sample 118' therefrom and to determine composition thereof.

The gauges 360a-c include a pressure indicator, a density meter (or densitometer), and a temperature gauge, respectively. While specific gauges are depicted, it will be appreciated that any number of sensors and/or gauges capable of measuring parameters of the sample 118' may be provided. Data from the chromatograph 358 and the gauges 360a-c may be passed to the controllers 136a,b.

The gauges 360a-c may be conventional temperature, pressure, or other gauges. The density meter 360b used for measuring the stream density of the sample 118' may be, for example, a high accuracy densitometer (e.g., as a Coriolis Effect density meter), a density measurement instrument (e.g., a vibrating cylinder densitometer, vibrating fork densitometer, radiation density meter, ultrasonic densitometer, displacement measurement meter, or liquid column differential pressure meter), and/or a density sampler (e.g., a cylinder weight measurement or displacement tester, such as a hydrometer).

Controller 136a may be used to collect and analyze data received from the chromatograph 358, gauges 360a-c, or other sources. For example, as shown in FIG. 1, other inputs, such as data from inspection 140a,b, may be fed into the controller 136a to analyze aspects of the production 100, such as the product, equipment and process. For example, production parameters, such as gas velocity, gas density, mass flow rate of cycle gas, percent of cycle gas condensed in the cooler, temperature, reliability indicators for the cycle gas compressor, fouling indicators for process equipment, raw material vent losses, etc., may also be monitored and/or inferred.

The controller 136a may collect, sort, analyze, and/or otherwise process the data into a usable form. Production data may be collected to confirm production operations, such as the reaction operation. For example, measurements from the chromatograph 358 may be collected by the controller 136a, and the data used to control production 100. The chromatograph 358 may be, for example, an online reactor chromatograph 358 that may provide readings to ensure that compositions of the reactor 104 are within predefined operating ranges needed to manufacture products within product specification limits, to calculate an accurate production rate where production rate cannot be measured directly, to determine composition changes needed to control and maximize production rate, to calculate operating parameters used to ensure the reactor is operated efficiently and reliably, and/or to determine purge gas flows needed in the resin purging section of plant. The chromatograph 358 may be used to control production by providing composition measurements to the controllers 136a,b that are used to selectively activate the valves 110a-d to adjust the flow of chemical components 110a-d, thereby altering the composition of the chemical mixture 118.

The monitor 134 is also provided with the gauges 360a-c to monitor the operation of the chromatograph 358. The controller 136a may also perform calculations to determine expected parameters of the chemical mixture 118 based on the compositions of the sample 118' determined by the chromatograph 358 and the measured parameters generated by the gauges 360a-c. In an example, the measured data, such as density from density meter 360b and composition detected by the chromatograph 358, may be combined using an equation-of-state to calculate expected parameters, such as an expected density, of the chemical mixture 118.

An equation-of-state is used to calculate various thermodynamic properties of multicomponent vapor and liquid mixtures such as the molar density, the ideal gas compressibility, molar enthalpy, and fugacity. For example, the following Benedict-Webb-Rubin (BWR) equation-of-state may be used to calculate molar density and the corresponding compressibility factor, molar enthalpy and fugacity coefficients of a multicomponent vapor or liquid mixture:

$$P = RT\rho + \left(B_0 RT - A_0 - \frac{C_0}{T^2}\right)\rho^2 + \\ (bRT - \alpha)\rho^3 + \alpha a\rho^6 + \frac{c\rho^3}{T^2}(1 + \gamma\rho^2)e^{-\gamma\rho^2}$$

Eqn. (1)

where P is absolute pressure, T is absolute temperature, R is the ideal gas constant, and ☐ is molar density. Bo, Ao, Co, a, b, c, ⌈, ⌈ are BWR Equation constants related to composition as follows:

$$x_m = [\Sigma(y_j x_j^{1/r})]^r$$

Eqn. (2)

where $X_m$ represents a BWR equation constant parameter for the mixture, xj is a BWR equation constant parameter for component j, yj is a mole fraction of component j in mixture, and r is the exponent value shown in the following table:

TABLE 1 exponent values

| Constant | r | Constant | r |
|---|---|---|---|
| Bo | 1 | b | 3 |
| Ao | 2 | c | 3 |
| Co | 2 | ⌊⌋ | 3 |
| a | 3 | ⌈ | 2 |

The constant parameter Co for each component is made to be a function of temperature. The temperature dependence is expressed as a polynomial in temperature as follows:

For $TLO_j \leq T \leq THI_j$ $$c_{0j}^{1/2} = CZ_j + Cl_j T + C2_j T^2 + C3_j T^3 + C4_j T^4 + C5_j T^5$$

Eqn. (3)

For $T > THI_j$ $$c_{0j}^{1/2} = CZ_j + Cl_j THI_j + C2_j THI_j^2 + C3_j THI_j^3 + C4_j THI_j^4 + C5_j THI_j^5$$

Eqn. (4)

For $T < TLO_j$ $$c_{0j}^{1/2} = CZ_j + Cl_j T + C2_j TLO_j (2T - TLO_j) + C3_j TLO_j^2 (3T - 2TLO_j) + C4_j TLO_j^3 (4T - 3TLO_j) + C5_j TLO_j^4 (5T - 4TLO_j)$$

Eqn. (5)

where CZj, C1j, . . . , C5j are constant parameters for component j, and TLOj, THIj are temperature limits on the Co equation for component j.

The term "equation-of-state" as used herein is any relation that relates mixture properties to composition. While the BWR equation-of-state is described above as an example relationship that may be used, it will be appreciated that other equations-of-state, such as the Redlich-Kwong equation-of-state may be used. Also, other methods that relate composition measurements to a secondary measurement may be used. A different relationship may be used if a different secondary measurement, such as heat capacity or viscosity, is provided. For example, the method of Ely and Hanley to calculate the viscosity of a multi-component mixture may be used if the measurement of the liquid viscosity is provided.

Once the expected parameters, such as density, are determined, the expected parameters may be compared with actual measurements taken by gauges 360a-c, such as actual density. Examples of techniques for monitoring and comparing data are provided in U.S. Pat. No. 8,032,328, previously incorporated by reference herein. Where the comparison shows that the actual and expected parameters are within an acceptable and/or predetermined range, then the production 100 may be validated. Where the comparison shows a difference outside acceptable and/or predetermined ranges, the controller 136b may be activated to make an adjustment to the production 100, for example, by adjusting one or more of the valves 110a-c to change the composition. Other corrections to the process may also be envisioned.

Controller 136b may be provided with software, such as APC+™ or UNIPOL UNIPPAC™ and/or logic, and associated hardware to implement commands based on the analyzed data. Controller 136b may receive raw and/or analyzed data from the controller 136a and/or from data sources, such as the chromatograph 358 and gauges 360a-c. The controller 136b may be coupled to various portions of the production 100 for implementing commands based on the data and according to predetermined logic. For example, the controller 136b may be coupled to valves 110a-d to selectively adjust the flow rate thereof based on measured and/or analyzed data, thereby controlling composition of the chemical components 110a-d and/or resin 118 generated therefrom. Examples of techniques for controlling a reactor are provided in U.S. Pat. Nos. 8,742,035 and 8,354,481, previously incorporated by reference herein.

Figure 4:
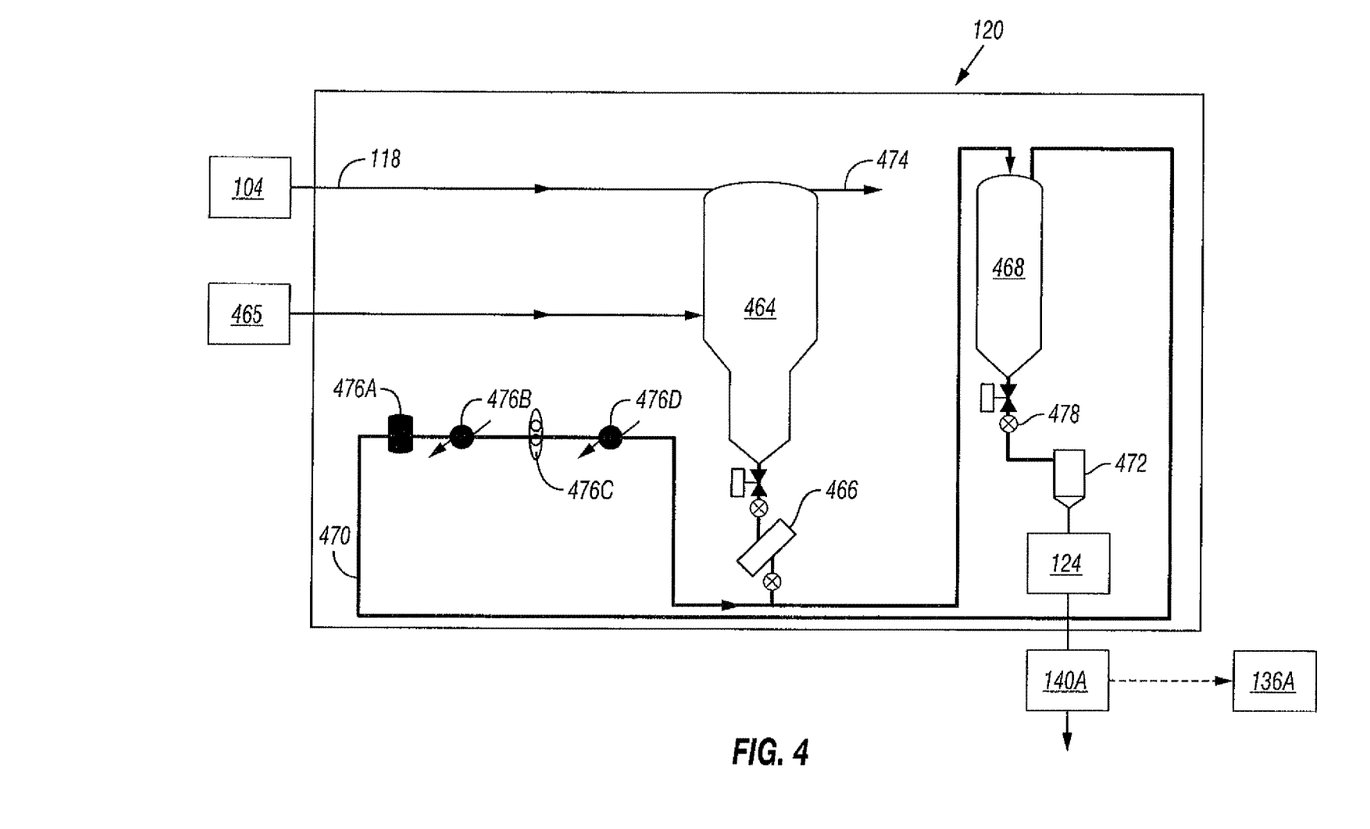
FIG. 4 is schematic diagram depicting a purger of FIG. 1 in greater detail.
Figure 5:
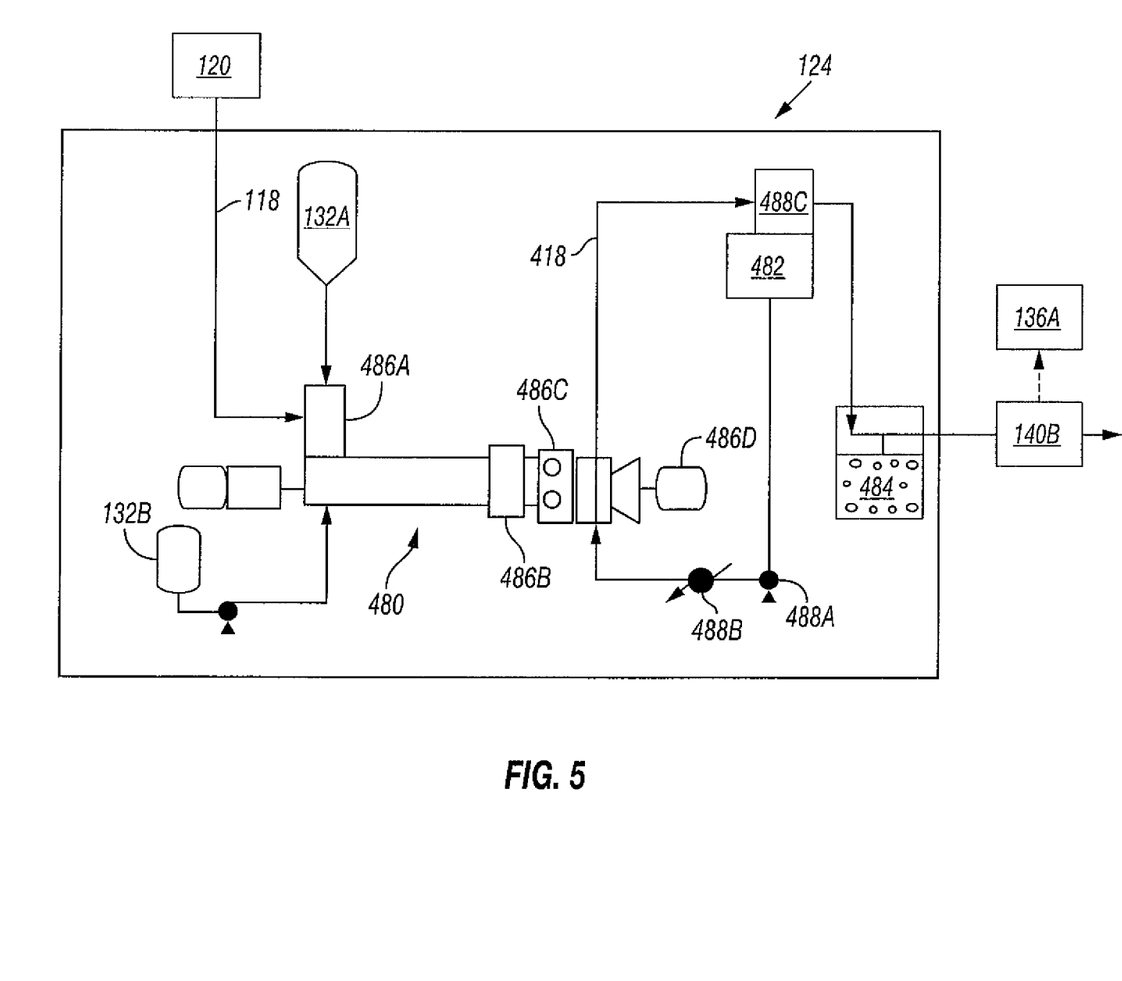
FIG. 5 is schematic diagram depicting a pelleter of FIG. 1 in greater detail.

FIGS. 4 and 5 show examples of portions of the packager 106 of FIG. 1. FIG. 4 shows purging by the purger 120 in greater detail. As shown in this Figure, the purging 120 includes a product purge bin 464, a screener 466, storage 468, a conveying system 470, and a hopper 472. Chemical mixture 118 from the reactor 104 is passed into the product purge bin 464 for storage. A chemical component 465, such as Nitrogen, may be applied to the product purge bin 464, and a portion of the chemical mixture 118 may be discharged by flare 474. The remaining chemical mixture 118 may be screened with screener 466.

The screened chemical mixture 118 may pass into intermediate storage 468. At least a portion of the screened chemical mixture 118 (e.g., a gas portion) may pass through the conveying system 470 and be recirculated back into the intermediate storage 468. The conveying system 470 may include various cooling components, such as filter 476a, cooling unit 476b, blower 476c, and aftercooler 476d. The stored chemical mixture 118 may be selectively passed by valve 478 into the surge hopper 472. The surge hopper 472 may selectively pass the chemical mixture 118 to other portions of the packaging 106, such as pelleter 124. As shown, inspection 140a may optionally be provided about the purging 120 to provide data or other inputs to the controller 136a.

FIG. 5 is a schematic diagram depicting pelleting 124 in greater detail. The purged chemical mixture 118 is passed from the purging 120 to the pelleting 124 for reshaping into a usable product. As shown, the pelleting 124 includes a feeder 480, a water tank 482, and loading bins 484. The feeder 480 includes a feed hopper 486a, gear pump 486b, screen pack 486c, and pellet unit 486d to transfer and shape the purged chemical mixture 118 into pellets 418. The dry additives 132a and liquid additives 132b are applied to form the pellets 418 along the feeder 480.

The pellets 418 are circulated through the water tank 482 and cooled by water circulated with a pump 488a and cooler 488b. A pellet dryer 488c is also provided to dry the pellets 418 before loading into load bins 484. The pellets 418 may be inspected at 140b and the data fed into the controller 136a.

Fault Detection and Validation

In operation, the monitor 134 may be used to monitor the production 100 as shown in FIGS. 1 and 3. Chemical components, such as purified reactant gasses (e.g., 108a,b) and catalyst (e.g., 112) are fed to the reactor 104 where polymer is generated. The composition of the reactant gas is measured using the chromatograph 358. Checks may also be done by the monitor 134 to validate the composition measurement. If validated, the composition measurements may be used as inputs to a controller (e.g., 136b) that adjusts the reactor feeds (e.g., intakes 110a-d, 116a,b) as needed to maintain reactant gas at the desired composition. A continuous polymerization process (e.g., production 100) may be carried out in the reactor 104 where the properties of the polymer product and the polymerization rate may be controlled by adjusting the composition of the chemical components (e.g., reactant gasses) 110a-d via valves 110a-d.

The monitor 134 may be used to validate the measurements taken by the chromatograph 358. This validation may be performed by taking actual measurements, such as the process stream density, for comparison with the expected measurements calculated based on measurements taken by the chromatograph 358. The stream density or other parameters may be measured using an instrument (e.g., gauges 360a-c) designed to such parameters. The composition measurements from the chromatograph 358, along with actual measurements, such as stream temperature and pressure, of the sample 118' may be analyzed in the controller 136a using a suitable equation-of-state, such as the BWR equation-of-state, to determine the expected parameters, such as stream density.

The calculated expected stream density value may be compared to the measured density reading to detect malfunction of the chromatograph 358. The measured density is compared to the expected density to determine if the discrepancy between the two values is within predefined limits. The results of the comparison analysis may also be used, for example, to trigger alarms, send appropriate messages, and/or perform automated actions using the controller 136b.

The limits are selected using statistical methods. The comparison may use an absolute or relative difference between the expected and measured density. The comparison may also detect potential errors using, for example, a limit check on these values, a limit check on the ratio of these values, established statistical process control methods, and/or a variety of fault detection methodologies using conventional techniques.

Use of the density meter readings provides a means to validate the readings from the chromatograph 358, and therefore adjust performance of the monitor 134. If there is little to no discrepancy between the measured and calculated density, the gas composition measurements are deemed accurate and are used as inputs to the controller 136b that maintains reactant gas composition by manipulating reactor feeds (e.g., 110*a-d*). Where a difference between the predicted and measured density is beyond a predetermined level, the difference may be an indication that a fault is detected.

If the check indicates the composition measurements may be erroneous (e.g., there is a discrepancy outside given limits), pre-determined manual and automated actions may be triggered. Manual actions that may be triggered include troubleshooting to determine the cause of the fault, replacing potentially plugged filters, recalibrating the chromatograph, checking the proper functionality of other instrument readings (e.g., pressure, temperature, and density), and checking for other problems that could cause erroneous composition measurement. Manual actions may also include procedures for manually operating the reactor 104, thereby eliminating the use of advanced process controls and calculations that may rely on erroneous chromatograph readings.

Automated control actions may also be initiated and alarms generated that trigger pre-determined intervention. Some examples of intervention may include: eliminating the use of chromatograph readings that caused the fault for control purposes, or using the last confirmed value taken from the chromatograph until the fault is eliminated. Automated steps may also include changing the gas composition controller mode to a degraded control state designed to keep the composition near target for a limited time in the absence of reliable composition measurements. In some cases, the production may be adjusted so that the amount of the chemical components may be input according to a pre-determined target (e.g., by controlling valves 110*a,b*) so that a predetermined composition is generated.

If the fault does not clear, use of the chromatograph for a higher level control may be automatically turned off (referred to as 'shedding control'). Such higher level controls may be advanced process control applications that control reactor production rate and resin product quality based on the measured composition. When these controls are shed, the underlying manipulated variables, such as reactor temperature, pressure and raw material feed rates, may be placed into a manual operating mode to avoid using the chromatograph 358 as a controller.

The analysis (e.g., comparison) performed during the monitoring may be further analyzed using other fault detection or analysis techniques, such as those involving evaluating historical data and predicted outputs, filtering of out of range deviations, stochastic modeling methods that perform a material balance around the reactor (e.g., for gas phase polyethylene plants), eliminating high and low values for analysis results, and/or detecting analyzer measurement results falling outside of the high and low limits. Examples of fault detection that may be used with the present monitoring are provided by APC+™ or UNIPOL™ software and related literature; Qingsong Yan, "Model-Based and Data Driven Fault Diagnosis Method With Applications to Process Monitoring," Case Western Reserve University, May 2004; and US Patent/Application No. 20130069792, U.S. Pat. Nos. 7,720,641, 8,121,817, 7,346,469, the entire contents of which are hereby incorporated by reference herein.

While the methods provided herein describe techniques relating to a chemical process, such as polymerization, it will be appreciated that the methods herein may be used with other chemical processes. Additionally, while primary measurements are described as composition measurements by a chromatograph and secondary measurements are described as density, such primary measurements may be performed by other composition detection devices, and such secondary measurements may be performed using gauges or devices capable of measuring various parameters, such as heat capacity, thermal conductivity, electrical conductivity, optical properties, etc.

EXAMPLE

A continuously operated polymerization process carried out in a gas phase fluidized bed reactor uses a titanium based catalyst to produce polyethylene. The monomers polymerized are ethylene and 1-hexene. The reactor was being operated with the total reactor pressure of about 270 psig (18.62 bar) and a reactor bed temperature of about 84° C. The approximate average reactor gas composition were 0.3 mol % hydrogen, 71 mol % nitrogen, 15 mol % ethylene, 1.0 mol % ethane, 0.4 mol % methane, 11.6 mol % isopentane, 0.5 mol % 1-hexene and 0.3 mol % other miscellaneous hydrocarbons. The measured sample gas density was 1.488 lbs/cuft (0.0238 g/cm3) and the expected density calculated using the Benedict Webb Rubin Equation of State was 1.446 lbs/cuft (0.0232 g/cm3). The ratio of these two densities was averaging 0.972. Statistical analysis of the density ratio showed that the ratio was expected to normally lie within the range from 0.965 to 0.985.

At one point, the composition measurements of isopentane, 1-hexene and nitrogen deviated from the average, changing to values of about 14.1 mol % isopentane, 0.7 mol % 1-hexene, and 68.0 mol % nitrogen. The calculated gas density using these measurements was 1.499 lbs/cuft (0.0240 g/cm3) and the measured density was 1.478 lbs/cuft (0.0237 g/cm3). The ratio of the two density values was 1.025 which was outside the normal expected limits.

Analyzer maintenance was performed and the composition of isopentane, 1-hexene, and nitrogen returned to near the average running values. The measured density remained at 1.478 lbs/cuft (0.0237 g/cm3), but the calculated density changed to 1.442 lbs/cuft (0.0231 g/cm3). The ratio of the two density values then was 0.976, a value within the normally expected range.

Figure 6:
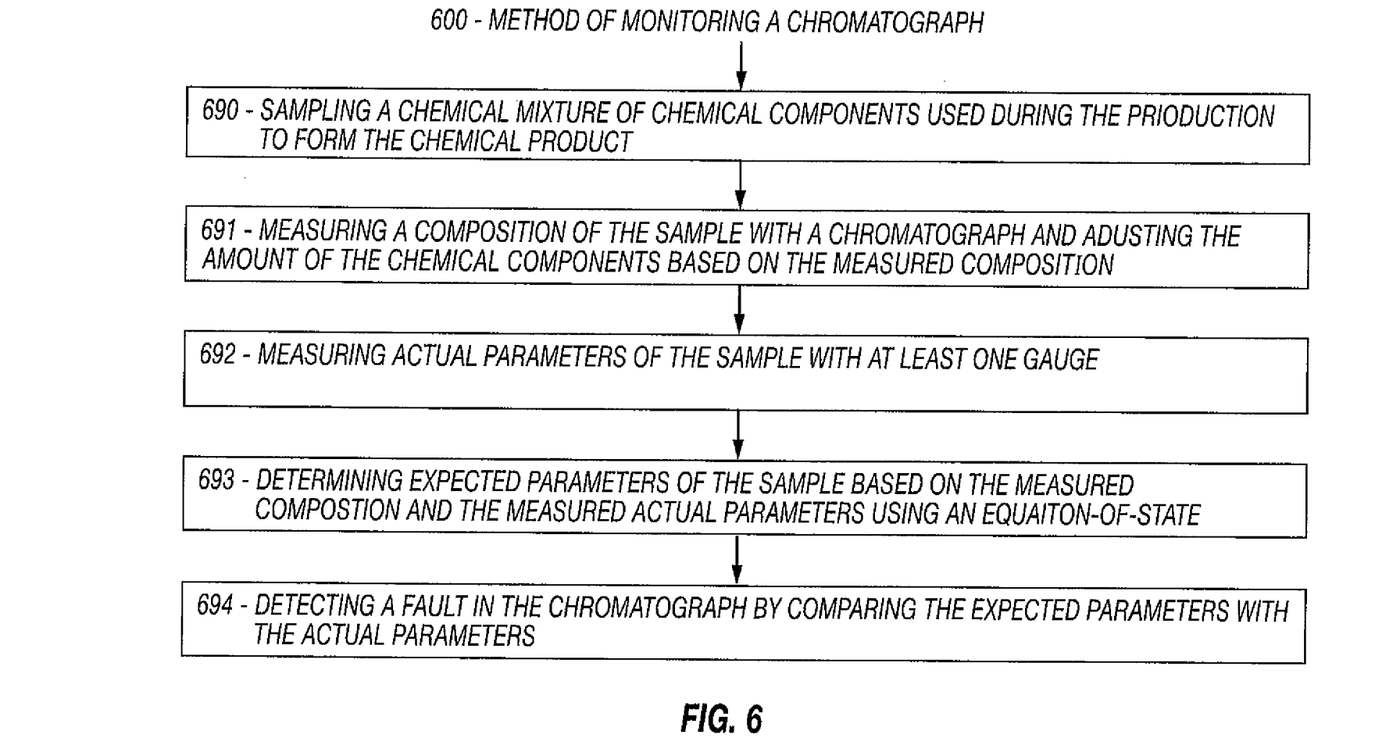
FIG. 6 is a flow chart depicting a method of monitoring production of a chemical product, involving monitoring a chromatograph.

FIG. 6 is a flow chart depicting a method 600 for monitoring a chromatograph used to control production of a chemical product, such as a polymer. The method involves 690—sampling a chemical mixture of chemical components used during the production to form the chemical product, 691—measuring a composition of the sample with a chromatograph and adjusting the amount of the chemical components based on the measured composition, 692—measuring actual parameters of the sample with at least one gauge, 693—determining expected parameters of the sample based on the measured composition and the measured actual parameters using an equation-of-state, and 694—detecting a fault in the chromatograph by comparing the expected parameters with the actual parameters.

The method may also involve, where a difference between the expected and actual parameters are within a predetermined range, validating the chromatograph based on the comparing; or where a difference between the expected and actual parameters are outside a predetermined range, selectively adjusting the chromatograph based on the comparing. The adjusting may involve ceasing the adjusting the amount of the chemical components based on the measured composition by the chromatograph, adjusting the amount of the chemical components according to a pre-determined target, and/or or re-calibrating the chromatograph. The method may be performed in any order and repeated as desired. A film may be produced by the method as described.

The present invention may be embodied in other forms without departing from the spirit and the essential attributes thereof, and, accordingly, reference should be made to the appended claims, rather than to the foregoing specification, as indicating the scope of the invention.

We claim:

1. A method for monitoring a chromatograph used to control production of a chemical product, the method comprising:
    sampling a chemical mixture of chemical components used during the production to form the chemical product;
    measuring a composition of the sample with a chromatograph and adjusting the amount of the chemical components based on the measured composition;
    measuring actual parameters of the sample with at least one gauge;
    determining expected parameters of the sample based on the measured composition and the measured actual parameters using an equation-of-state; and
    detecting a fault in the chromatograph by comparing the expected parameters with the actual parameters.

2. The method of claim 1, wherein the equation-of-state is Benedict-Webb-Rubin equation.

3. The method of claim 1, further comprising, where a difference between the expected and actual parameters are within a predetermined range, validating the chromatograph based on the comparing.

4. The method of claim 1, further comprising, where a difference between the expected and actual parameters are outside a predetermined range, selectively adjusting the chromatograph based on the comparing.

5. The method of claim 4, wherein the selectively adjusting comprises ceasing the adjusting the amount of the chemical components based on the measured composition by the chromatograph and adjusting the amount of the chemical components according to a pre-determined target.

6. A method for monitoring production of a chemical product formed from chemical components, the method comprising:
    forming a chemical mixture by passing the chemical components through a reactor;
    controlling the forming, the controlling comprising:
        collecting a sample of the chemical mixture during the forming;
        determining a composition of the sample with a chromatograph during the forming; and
        adjusting the passing of at least one of the chemical components through the reactor based on the determining; and
    monitoring the controlling, the monitoring comprising:
        measuring actual parameters of the sample;
        determining expected parameters of the sample based on the determined composition and the measured actual parameters using an equation-of-state;
        comparing the expected parameters with the actual parameters of the sample; and
        adjusting the controlling based on the comparing.

7. The method of claim 6, further comprising recirculating the chemical mixture through the reactor.

8. The method for claim 6, further comprising packaging the chemical mixture, the packaging comprises purging, granular handling, pelleting, adding additives, pellet binding, and loading.

9. The method for claim 6, wherein the adjusting comprises selectively adjusting the determined composition by adjusting a flow rate of the at least one of the chemical components and the catalyst.

10. A method for monitoring production of a chemical product, the method comprising:
    forming a chemical mixture by passing chemical components through a reactor; and
    controlling production of a chemical product, the controlling comprising:
        sampling a chemical mixture of chemical components used during the production to form the chemical product;
        measuring a composition of the sample with a chromatograph; and
        adjusting the amount of the chemical components based on the measured composition;
    detecting fault in the chromatograph, the detecting comprising:
        measuring actual parameters of the sample with at least one gauge;
        determining expected parameters of the sample based on the measured composition and the measured actual parameters using an equation-of-state; and
        comparing the expected parameters with the actual parameters; and
    adjusting the controlling based on the detecting.

* * * * *